United States Patent [19]

Adams

[11] Patent Number: 4,905,686
[45] Date of Patent: Mar. 6, 1990

[54] COLD WEATHER BREATHING MASK

[75] Inventor: Wilbur R. Adams, Terre Haute, Ind.

[73] Assignee: Simulators Limited, Inc., Terre Haute, Ind.

[21] Appl. No.: 143,002

[22] Filed: Jan. 12, 1988

[51] Int. Cl.⁴ ............................................. A61M 16/00
[52] U.S. Cl. .......................... 128/204.17; 128/206.21; 128/207.12
[58] Field of Search ...................... 128/204.17, 203.26, 128/203.27, 206.21, 207.12

[56] References Cited

U.S. PATENT DOCUMENTS

| Re. 20,135 | 10/1936 | Bjurstrom | 128/204.17 |
|---|---|---|---|
| 119,748 | 10/1871 | Duncanson | 128/204.17 |
| 443,191 | 12/1890 | Illing | 128/204.17 |
| 2,344,920 | 3/1944 | Maggi | 128/204.17 |
| 2,416,411 | 2/1947 | Sharbaugh et al. | 128/204.17 |
| 2,445,347 | 7/1948 | Ehlinger | 128/203.27 |
| 2,695,020 | 11/1954 | Glidden | 128/204.17 |
| 2,784,714 | 3/1957 | Pitzipio | 128/204.17 |
| 2,868,195 | 1/1959 | Finken | 128/204.17 |
| 4,062,359 | 12/1977 | Geaghan | 128/204.17 |
| 4,150,671 | 4/1979 | Tiger | 128/201.13 |
| 4,245,631 | 1/1981 | Wilkinson et al. | 128/204.17 |
| 4,601,287 | 7/1986 | Royce, Jr. | 128/204.17 |
| 4,620,537 | 11/1986 | Brown | 128/201.13 |

FOREIGN PATENT DOCUMENTS 0620266 7/1978 U.S.S.R. ............ 128/204.17
2077122A 12/1981 United Kingdom .

OTHER PUBLICATIONS

Cold Mask Advertised in Undated Dr. Leonard's Health Care Catalog received in the mail in approximately Dec., 1988.

Primary Examiner—Edgar S. Burr
Assistant Examiner—Aaron J. Lewis
Attorney, Agent, or Firm—Howrey & Simon

[57] ABSTRACT

A lightweight face mask for heating surrounding air to be inhaled by a user includes a thin cup-shaped inner shell and an outer shell spaced from and surrounding the inner shell, the inner and outer shells defining a preheating chamber therebetween through which air passes in a counter-current flow pattern before entering a user breathing space inside the inner shell. The mask may include an electric heating element and battery power supply for additionally heating air entering the user breathing space.

16 Claims, 3 Drawing Sheets

COLD WEATHER BREATHING MASK

BACKGROUND OF THE INVENTION

This invention relates to face masks, and is specifically directed to an improved means for warming cold air prior to inhalation by a mask user.

Inhaling cold air into the respiratory tract can be detrimental to the health of persons suffering from emphysema, asthma, angina and various other ailments. In cold weather, persons suffering from such ailments must either avoid breathing cold air altogether or take precautions to heat cold air before it is breathed. In addition, persons of good health working and exercising in frigid climates must take precautions against excessive heat loss due to the inhalation of frigid air.

A variety of apparatuses have been employed in the past to overcome the ill effects of breathing cold air. These range from simple scarfs to complex breathing masks and are employed to preheat cold air before inhalation. Most of these devices, however, either do not sufficiently preheat the cold surrounding air before breathing or are complex, cumbersome and prohibitively expensive. Several such breathing apparatuses are disclosed in the following patents: U.S. Pat. Nos. 4,150,671; 4,601,287; and 4,620,537. These mask apparatuses attempt to preheat air with battery powered heating elements or heat exchange devices. However, existing masks with heating elements have been inconvenient to use under normal use conditions because large, poorly located battery power supplies are either separate from the mask and require additional means for transport or are located within the mask breathing space where the battery is exposed to high moisture levels and where a user would be subjected to dangers from battery corrosion or battery fumes.

Another problem experienced with existing masks having heating elements is that a large amount of power is required to directly heat cold surrounding air. There have been attempts to reduce mask heating element power requirements by passing inhaled and exhaled air through heat absorbing material so as to preheat incoming air with heat stored from exhaled air before the incoming air reaches the heating element. However, these designs have the problems that some previously exhaled air is inhaled again and that exhaled air passes across the heating element where it is heated before being exhausted to the surrounding atmosphere.

In the mask disclosed in U.S. Pat. No. 4,150,671, air is preheated with a complex heat exchanger device having separate intake and exhaust passages rather than with a heating element. Thus, the problem of rebreathing exhaled air is overcome, but the heat exchange device is so complex that it cannot be economically manufactured. It is also difficult for such exchangers to sufficiently heat frigid air.

OBJECTS OF THE INVENTION

Accordingly it is an object of the invention to provide a cold weather breathing mask that is both compact and inexpensive to produce.

It is another object of the invention to provide a cold weather breathing mask that preheats incoming air with heat from exhaled air without the risk of rebreathing large quantities of oxygen deficient exhaled air.

A further object of the invention is to provide a cold weather breathing mask with a heating element for heating incoming air that does not waste energy heating exhaled air being discharged to the atmosphere.

Yet another object of the invention is to provide a cold weather heating mask that efficiently exchanges heat between exhaled air and incoming air before the incoming air is heated by a heating element so as to enable a high degree of air heating without consuming excessive battery power.

Additional objects and advantages of the present invention will be set forth in part in the description that follows and in part will be obvious from the description or may be learned by practice of the invention. The objects and advantages of the invention may be realized and obtained by the apparatus particularly pointed out in the appended claims.

SUMMARY OF THE INVENTION

To achieve the objects and in accordance with the purpose of the invention, as embodied and as broadly described herein, a lightweight face mask for heating surrounding air to be inhaled by a user is provided. The mask comprises a thin, cup-shaped inner shell having a concave inner surface, a convex outer surface, and a user abutment portion where the inner and outer surfaces meet, the abutment portion being adapted to seal against the user's face around the user's mouth and nose with the concave inner surface defining a user breathing space; an outer shell spaced from and surrounding the convex outer surface of the inner shell, the inner and outer shells being joined along the user abutment portion and defining an air preheating chamber there between; inlet port means in the outer shell having first valve means for permitting entry of surrounding air into the preheating chamber and for preventing exit of air from the preheating chamber to the surrounding air; an air passage in the inner shell for passing air between the preheating chamber and the user breathing space; channel means in the preheating chamber for directing air entering the preheating chamber through the first port means over substantially the entire convex outer surface of the inner shell before passing through the air passage; and exhaust port means in the inner and outer shells having second valve means for permitting exit of air directly from the breathing space to the surrounding air and for preventing entry of surrounding air into the user breathing space. The mask may further include an air heating element for heating air in the passage passing from the preheating chamber to the user breathing space, and a battery power supply for electrically contacting the heating element. Preferably air passing through the mask preheating chamber follows a counter-current flow pattern in passing over the convex outer surface of the inner shell.

The accompanying drawings, which are incorporated in and constitute a part of this specification, illustrate the presently preferred embodiment of the invention and, together with the description, serve to explain the principles of the invention.

DESCRIPTION OF THE PREFERRED EMBODIMENT

Figure 1:
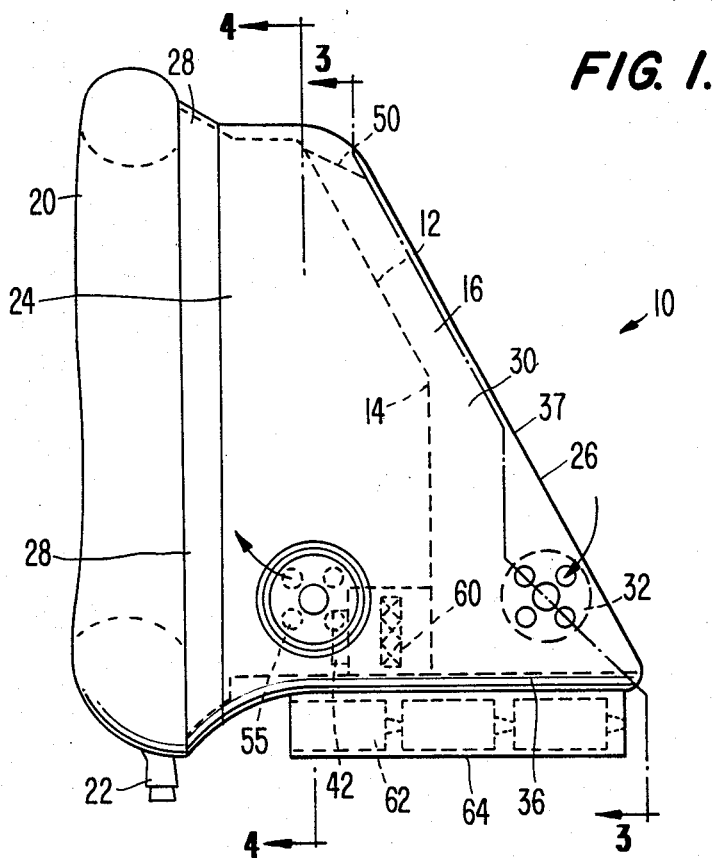
FIG. 1 is a side elevational view of a cold weather breathing mask in accordance with the present invention.

Reference will now be made in detail to the presently preferred embodiment of the invention, an example of which is illustrated in the accompanying drawings. Throughout the drawings, like reference characters are used to designate like elements.

In FIG. 1, a cold weather breathing mask 10 is illustrated. Mask 10 is a lightweight face mask for heating surrounding air to be inhaled by a user. Mask 10 is preferably made of a lightweight moldable plastic material, as for example Polyethylene Terephthalate (PET) or Co-Polyester Glycol Modified PET (PETG), but may also be made of a lightweight metal or composite material. It should also be recognized that the mask may be made of some combination of the above materials.

According to the invention, mask 10 includes a thin cup-shaped inner shell having a concave inner surface and a convex outer surface and a user abutment portion where the inner and outer surfaces meet. The abutment portion is adapted to seal against the user's face such that the cup-shape inner shell covers the user's mouth and nose.

Figure 2:
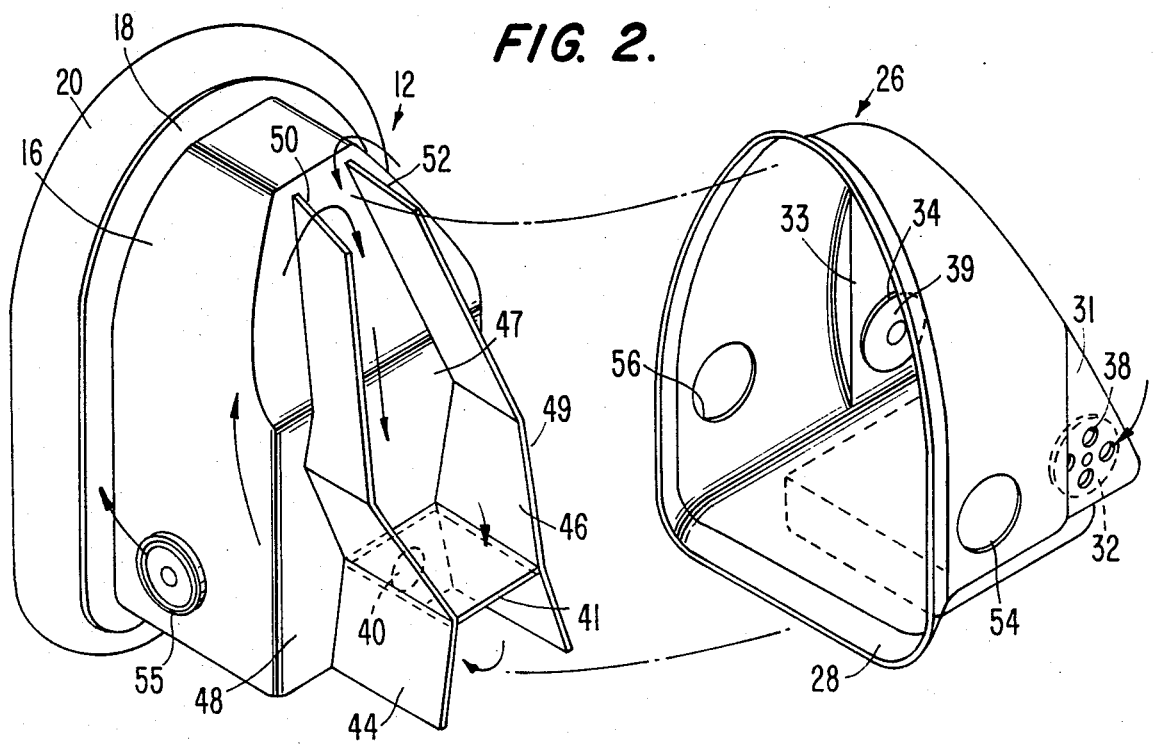
FIG. 2 is an exploded perspective view of the cold weather breathing mask of FIG. 1.

As embodied herein, and as best shown in FIGS. 1 and 2, inner shell 12 is generally cup-shaped with a concave inner surface 14 and a convex outer surface 16. A user abutment portion 18 defines a rim of inner shell 12 where inner surface 14 and outer surface 16 meet.

Abutment portion 18 is adapted to seal against the mask user's face around the user's mouth and nose. A face seal is affixed to the abutment portion for sealing the mask against the user's face. The face seal may comprise a pliable inflated continuous tube 20 affixed to abutment portion 18. Tube 20 has a corked valve stem 22 through which tube 20 may be inflated. It is anticipated that other seals may be utilized in place of tube 20, as for example, a styrofoam ring or a rubber gasket. Concave inner surface 14 of inner shell 12 defines a user breathing space 24 that seals against the user's face when sealing tube 20 is pressed against the user's face.

Figure 5:
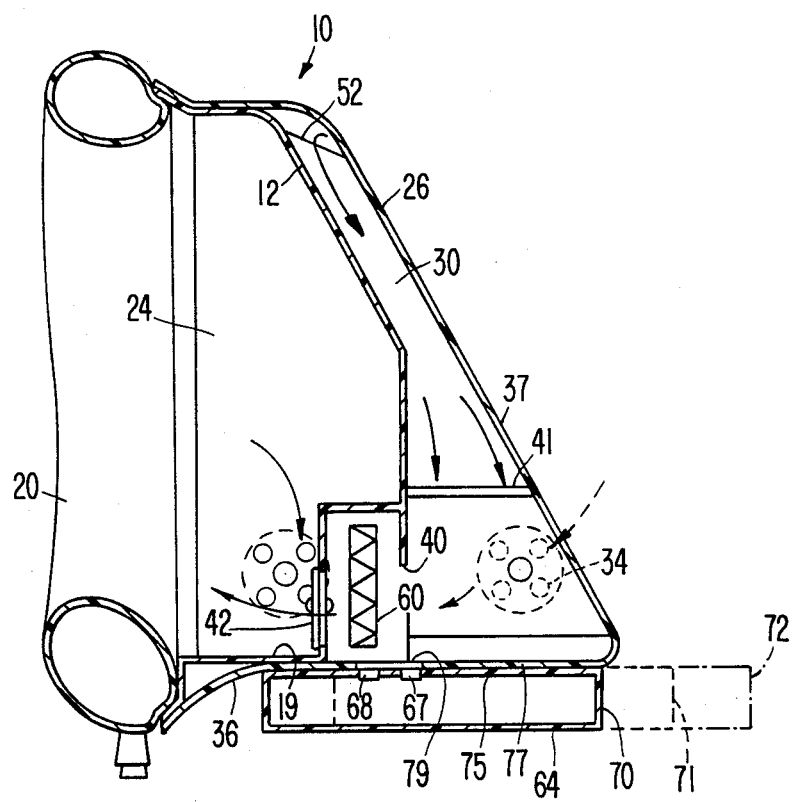
FIG. 5 is a cross-sectional view taken along the line 5—5 of FIG. 3.

According to the invention, an outer shell is spaced from and surrounds the convex outer surface of the inner shell. The inner and outer shells are joined along the user abutment portion and define an air preheating chamber there between. As embodied herein, an outer shell 26 is spaced from and surrounds outer surface 16 of inner shell 12. Outer shell 26 has a rim 28 that joins abutment portion 18 of inner shell 12. When rim 28 is joined and sealed with abutment portion 18, an air preheating chamber 30, as best shown in FIGS. 1 and 5, is formed between inner shell 12 and outer shell 26.

According to the invention, there is provided inlet port means in the outer shell having first valve means for permitting entry of surrounding air into the preheating chamber and for preventing exit of air from the preheating chamber to the surrounding air. As embodied herein ports 32 and 34 penetrate opposite side surfaces 31 and 33 of outer shell 26. Preferably ports 32 and 34 penetrate surfaces 31 and 33 close to where side surfaces 31 and 33 join a bottom surface 36 of outer shell 26. Outer shell side surfaces 31 and 33 are joined by a front surface 37 of outer shell 26. Front surface 37 also joins bottom surface 36.

Ports 32, 34 have valves 38, 39, respectively, fixed therein. Valves 38 and 39 are one-way valves that permit entry of surrounding air into preheating chamber 30 and prevent exit of air from preheating chamber 30 to the surrounding air. Valves 38 and 39 may comprise any type one-way valve as, for example, check valves or flapper valves.

According to the invention, an air passage in the inner shell for passing air between the preheating chamber and user breathing space is provided. As embodied herein, a passage 40 penetrates a front surface 17 of inner shell 12 at a central portion of front surface 17. Passage 40 penetrates front surface 17 near where front surface 17 joins a bottom surface 19 of inner shell 12. A valve 42 may be fixed in passage 40 such that valve 42 permits air to enter user breathing space 24 from preheating chamber 30 while preventing exit of air from user breathing space 24 to preheating chamber 30. Valve 42 is a one-way valve, such as a check valve or flapper valve. When a user exhales into breathing space 24, valve 42 and/or valves 38 and 39 prevent air from passing in a reverse direction through passage 40 and breathing chamber 30.

According to the invention, there is provided channel means in the preheating chamber for directing air entering the preheating chamber through the inlet ports over substantially the entire convex outer surface of the inner shell before passing through the air passage. As embodied herein, channel dividers 44 and 46 extend out from front surface 17 of inner shell 12. Dividers 44 and 46 abut against front surface 37 and bottom surface 36 of outer shell 26. Dividers 44 and 46 divide preheating chamber 30 into a central vertical subchamber 47 and first and second side vertical subchambers 48, 49 on opposite sides of central subchamber 47. Central subchamber 47 may have an air filter 41 removably mounted between dividers 44 and 46, for those breathing situations in which air filtering is beneficial to a mask user. Side subchambers 48, 49 included those portions of breathing space 30 on either side of inner shell 12. Dividers 44, 46 have ends 50, 52, respectively, that do not abut outer shell 26. First and second vertical side chambers 48, 49 communicate with central subchamber 47 through passages formed between divider ends 50, 52 and outer shell 26, the passages being at the ends of the vertical subchambers opposite bottom surface 36 of outer shell 26. Accordingly, air entering preheating chamber 30 through ports 32 and 34 must travel the length of one of the side chambers 48, 49 and the length of central subchamber 47 in a counter-current flow pattern before entering air passage 40. Thus, cold air in preheating chamber 30 is exposed to and warmed by the entire outer surface of inner shell 12 before entering user breathing space 24 through passage 40.

According to the invention, there is provided exhaust port means in the inner and outer shells. As embodied herein, outer shell 26 includes ports 54, 56 which align and seal with ports 55, 57, respectively, of inner shell 12. Thus, air can pass from user breather space 24 to the surrounding atmosphere through ports 54, 55 and 56, 57 without reentering preheating chamber 30.

According to the invention, the exhaust ports in the inner and outer shells have valve means therein for permitting exit of air directly from the breathing space to surrounding air and for preventing entry of surrounding air into the user breathing space. As embodied herein, exhaust ports 54, 55 and 56, 57 each have a one-way valve, such as a check valve or flapper valve, fitted therein that permits air to exit from breathing space 24 while not permitting air intake through ports 54, 55 and 56, 57. Thus, when a user inhales air from breathing space 24, all inhaled air enters through preheating chamber 30, and when a user exhales air into user breathing space 24, the exhaled air is exhausted directly from user breathing space 24 through ports 54, 55 and 56, 57.

Figure 3:
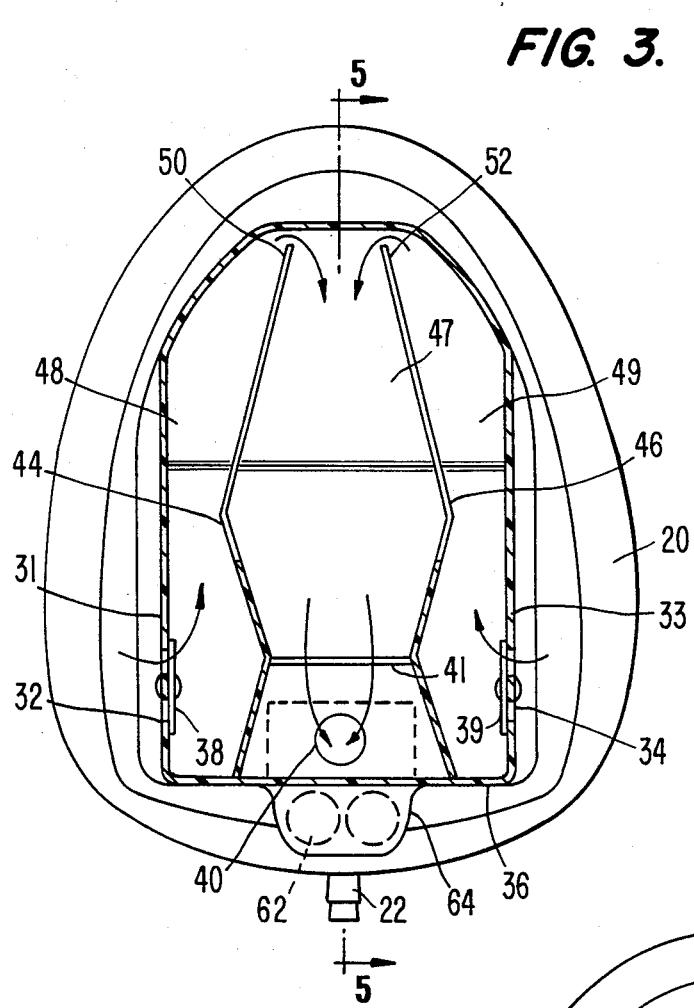
FIG. 3 is a cross-sectional view taken along the line 3—3 of FIG. 1.
Figure 4:
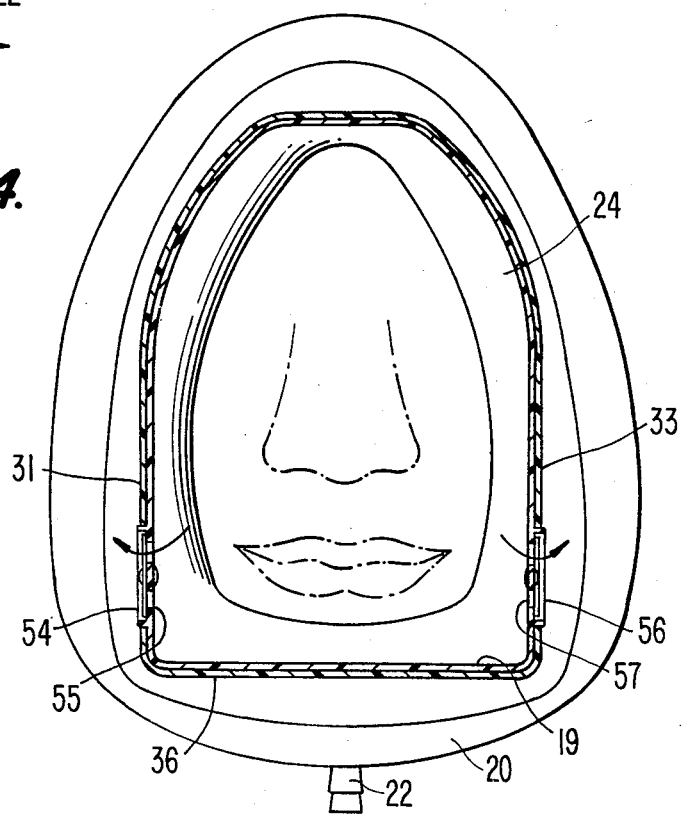
FIG. 4 is a cross-sectional view taken along the line 4—4 of FIG. 1.

According to the preferred embodiment of the invention, a heating means for heating air in the passage from the preheating chamber to the user breathing space is provided. As embodied herein, the heating means includes an electric heating element 60 in passage 40, as best shown in FIG. 5. Electric heating element 60 is preferably a conductive heating coil removably mounted in passage 40. Electric heating element 60 is preferably powered by a battery power supply in electrical contact with heating element 60. The battery supply is preferably embodied as a plurality of rechargeable batteries 62 in a compartment 64 on an outside surface of outer shell 26, as shown in FIGS. 3 and 5.

Figure 6:
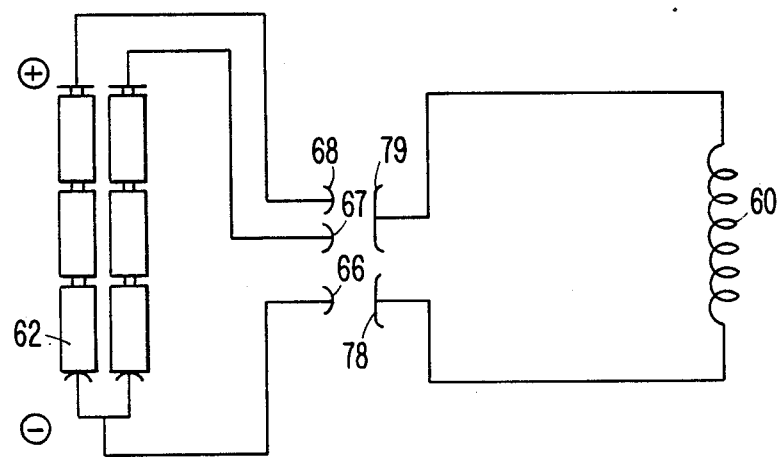
FIG. 6 is a diagram of an electric circuit for electrically connecting the heating element and power supply of the cold weather breathing mask of FIG. 1.

Preferably, battery compartment 64 is slide mounted on outer shell 26 so as to be slidable between positions 70, 71 and 72 (FIG. 5). Electrical contacts 66, 67 and 68 on a top surface 75 of compartment 64 are electrically connected to rechargeable batteries 62, as shown in FIG. 6. Electrical contacts 78 and 79 on a bottom surface 77 of outer shell 26 are electrically connected to heating element 60. When compartment 64 is moved to position 70, contacts 67 and 68 touch contact 79 while contact 66 touches contact 78, such that heating element 60 is powered by all of the batteries 62. When compartment 64 is moved to position 71, contacts 68 and 79 touch as do contacts 66 and 78, such that heating element 60 is powered by only half of the batteries 62. When compartment 64 is moved to positions 72, no contacts touch such that heating element 60 is not powered. Thus, when cool air needs only mild heating, as is provided by preheating chamber 30, compartment 64 is moved to "OFF" position 72. When greater heating, but not maximum heating, is required, compartment 64 is moved to "INTERMEDIATE" position 71 wherein incoming air is heated by both preheating chamber 30 and heating element 60. When maximum heating is desired, compartment 64 is moved to "FULL" position 70 such that heating element 60 is in electrical contact with all rechargeable batteries 62 and air preheated in preheating chamber 30 is maximally heated by electric heating element 60. Thus, an appropriate level of air heating and battery power usage is obtained. Of course, it is to be realized that other power supplies, such as disposable AA batteries could alternatively be utilized in place of rechargeable batteries 62. It is also anticipated that a heavy duty auxiliary power supply could be used in place of rechargeable batteries 62 in extreme weather conditions.

In operation, a user desiring air heating places cold weather breathing mask 10 over his mouth and nose such that user breathing space 24 is sealed against the user's face by sealing tube 20. The user may attach mask 10 in place by means of an elastic, velcro or other equivalent strap. Next, the user can adjust the position of compartment 64 depending upon how much air heating is desired. Upon inhalation, air enters preheating chamber 30 via ports 32 and 34 and passes in a counter-current flow pattern over the outer convex surface of inner shell 12 from which heat from previously exhaled air is absorded. Air then passes through chamber 40 and heating element 60 before entering the user's respiratory tract. Upon exhalation, air is breathed into user breathing space 24 from which heat in the exhaled air is transferred to inner shell 12 for transfer to air that will pass through subchamber 30. Exhaled air is exhausted through exhaust ports 54, 55 and 56, 57 directly without again contacting heating element 60.

It will be apparent to those skilled in the art that modifications and variations can be made in the cold weather breathing mask of this invention. The invention in its broader aspects is, therefore, not limited to the specific details, representative apparatus, and illustrative example shown and described herein above. Thus, it is intended that all matter contained in the foregoing description or shown in the accompanying drawings shall be interpreted as illustrative and not in a limiting sense.

What is claimed:

1. A lightweight face mask for heating surrounding air to be inhaled by a user, said mask comprising:

a thin cup-shaped inner shell having a concave inner surface, a convex outer surface and a user abutment portion where said inner and outer surfaces meet, said abutment portion adapted to seal against the user's face around the user's mouth and nose with said concave inner surface defining a user breathing space;

an outer shell spaced from and surrounding said convex outer surface of said inner shell, said inner and outer shells being joined along said user abutment portion and defining an air preheating chamber there between;

inlet port means in said outer shell having first valve means for permitting entry of surrounding air into said preheating chamber and for preventing exit of air from said preheating chamber to surrounding air;

an air passage in said inner shell for passing air between said preheating chamber and said user breathing space;

intermediate valve means in said air passage for permitting air to enter said user breathing space from said preheating chamber and for preventing exit of air from said user breathing space to said preheating chamber;

channel means in said preheating chamber for directing air entering said preheating chamber through said inlet port means over substantially the entire convex outer surface of said inner shell before passing through said air passage thereby heating the air entering said preheating chamber; and exhaust port means in said inner and outer shells having second valve means for permitting exit of air directly from said breathing space to surrounding air and for preventing entry of surrounding air into said user breathing space.

2. The face mask according to claim 1, further comprising air heating means for heating air in said passage passing from said preheating chamber to said user breathing space.

3. The face mask according to claim 2 wherein said heating means comprises an electric heating element in said passage.

4. The face mask according to claim 3 wherein said heating means further comprises a battery power supply for electrically contacting said electric heating element.

5. The face mask according to claim 4 wherein such battery power supply is affixed in a compartment on an outside surface of said outer shell.

6. The face mask according to claim 5 wherein said battery power supply comprises a plurality of rechargeable batteries.

7. The face mask according to claim 5 further comprising electric contact means for controlling electric contact between said battery power supply and said electric heating element, said switch means having an OFF position wherein said battery power supply and said heating element are not in electrical contract, a FULL position wherein said battery power supply is in complete electric contact with said heating element, and an INTERMEDIATE position wherein said battery power supply is in partial electric contact with said heating element.

8. The face mask according to claim 2 further comprising an air filter removeably mounted in said air passage.

9. The face mask according to claim 2 wherein said outer shell includes a front surface, two side surfaces connected to opposite sides of said front surface, and a bottom surface connected to bottom portions of said front and side surfaces, said inlet port means includes two valve ports, one of said ports passing through each of said side surfaces proximate said bottom surface, said air passage in said inner shell is proximate said outer shell bottom surface, and said channel means divides said preheating chamber into a central vertical subchamber in direct communication with said air passage, and first and second side vertical subchambers on opposite sides of said central subchamber, said first and second side vertical subchambers being in communication with one of said two valve ports, said first and second side vertical subchambers being in communication with said central vertical subchamber only at the ends of said subchambers opposite said bottom surface, whereby air entering said preheating chamber through said two valve ports must travel the length of one of said side vertical subchambers and of said central vertical subchamber in a counter-current flow pattern before entering said air passage.

10. The face mask according to claim 2 further comprising face sealing means fixed to said abutment portion for sealing said breathing chamber against a user's face.

11. The face mask according to claim 10 wherein said face sealing means comprises a pliable inflated continuous tube sealingly affixed to said abutment portion.

12. The face mask according to claim 10 wherein said face sealing means comprises a pliable rubber gasket sealingly affixed to said abutment portion.

13. The face mask according to claim 2 wherein said first and second valve means each comprise a check valve in said port means.

14. The face mask according to claim 2 wherein said first and second valve means each comprise a flapper valve in said port means.

15. A lightweight face mask for heating surrounding air to be inhaled by a user, said mask comprising:

a thin cup-shaped inner shell having a concave inner surface, a convex outer surface and a user abutment portion where said inner and outer surfaces meet, said abutment portion adapted to seal against the user's face around the user's mouth and nose with said concave inner surface defining a user breathing space;

an outer shell spaced from and surrounding said convex outer surface of said inner shell, said inner and outer shells being joined along said user abutment portion and defining an air preheating chamber there between;

inlet port means in said outer shell having first valve means for permitting entry of surrounding air into said preheating chamber and for preventing exit of air from said preheating chamber to surrounding air;

an air passage in said inner shell for passing air between said preheating chamber and said user breathing space;

air heating means for heating air in said passage passing from said preheating chamber to said user breathing space;

second valve means in said air passage for permitting air to enter said user breathing space from said preheating chamber and for preventing exit of air from said user breathing space to said preheating chamber;

channel means in said preheating chamber for directing air entering said preheating chamber through said inlet port means over substantially the entire convex outer surface of said inner shell before passing through said air passage; and exhaust port means in said inner and outer shells having third valve means for permitting exit of air directly from said breathing space to surrounding air and for preventing entry of surrounding air into said user breathing space.

16. A lightweight face mask for heating surrounding air to be inhaled by a user, said mask comprising:

a thin cup-shaped inner shell having a concave inner surface, a convex outer surface and a user abutment portion where said inner and outer surfaces meet, said abutment portion adapted to seal against the user's face around the user's mouth and nose with said concave inner surface defining a user breathing space;

an outer shell spaced from and surrounding said convex outer surface of said inner shell, said inner and outer shells being joined along said user abutment portion and defining an air preheating chamber there between, said outer shell including a front surface, two side surfaces connected to opposite sides of said front surface, and a bottom surface connected to bottom portions of said front and side surfaces, an inlet valve port in said outer shell, said inlet valve port passing through one of said outer shell side surfaces proximate said bottom surface for permitting entry of surrounding air into said preheating chamber and for preventing exit of air from said preheating chamber to surrounding air;

an air passage in said inner shell for passing air between said preheating chamber and said user breathing space, said air passage being proximate said outer shell bottom surface;

channel means in said preheating chamber for directing air entering said preheating chamber through said inlet valve port over substantially the entire convex outer surface of said inner shell before passing through said air passage thereby heating the air entering said preheating chamber, said channel means dividing said preheating chamber into a first vertical subchamber in direct communication with said air passage, and a second vertical subchamber, in communication with said inlet valve port, said second vertical subchamber being in communication with said first vertical subchamber only at the ends of said first and second vertical subchambers opposite said outer shell bottom surface, whereby air entering said preheating chamber through said valve port must travel the length of said second vertical subchamber and of said first vertical subchamber in a counter-current flow pattern before entering said air passage; and exhaust port means in said inner and outer shells having valve means for permitting exit of air directly from said breathing space to surrounding air and for preventing entry of the surrounding air into said user breathing space.

* * * * *